(12) United States Patent
Lasher et al.

(10) Patent No.: US 11,400,015 B2
(45) Date of Patent: Aug. 2, 2022

(54) KIT COMPRISING AT LEAST TWO BAGS

(71) Applicants: Fresenius Medical Care Deutschland GmbH, Bad Homburg (DE); Fresenius Medical Care Holdings, Inc., Waltham, MA (US); Fresenius Medical Care R&D (Shanghai) Co., Ltd., Shanghai (CN)

(72) Inventors: Richard Allen Lasher, Farmington, UT (US); Guangming Wu, Shanghai (CN); Zhengxin Ma, Shanghai (CN); Mingtao Gong, Shanghai (CN)

(73) Assignees: Fresenius Medical Care Deutschland GmbH, Bad Homburg (DE); Fresenius Medical Care Holdings, Inc., Waltham, MA (US); Fresenius Medical Care R&D (Shanghai) Co., Ltd., Shanghai (CN)

( * ) Notice: Subject to any disclaimer, the term of this patent is extended or adjusted under 35 U.S.C. 154(b) by 850 days.

(21) Appl. No.: 16/312,524

(22) PCT Filed: Jun. 29, 2016

(86) PCT No.: PCT/CN2016/087780
§ 371 (c)(1),
(2) Date: Dec. 21, 2018

(87) PCT Pub. No.: WO2018/000283
PCT Pub. Date: Jan. 4, 2018

(65) Prior Publication Data
US 2019/0159967 A1      May 30, 2019

(51) Int. Cl.
*A61J 1/10*      (2006.01)
*A61M 1/28*      (2006.01)

(52) U.S. Cl.
CPC .............. *A61J 1/10* (2013.01); *A61M 1/28* (2013.01); *A61M 1/287* (2013.01); *A61M 1/282* (2014.02)

(58) Field of Classification Search
CPC ............ A61J 1/10; A61M 1/28; A61M 1/282; A61M 1/284; A61M 1/285; A61M 1/287
See application file for complete search history.

(56) References Cited

U.S. PATENT DOCUMENTS 4,630,727 A * 12/1986 Feriani ................ A61M 1/3455
                                                    206/221
5,843,049 A * 12/1998 Heilmann .............. A61M 1/28
                                                    604/275
(Continued)

FOREIGN PATENT DOCUMENTS

CN      1185746      6/1998
CN      2647329      10/2004
(Continued)

OTHER PUBLICATIONS

International Search Report and Written Opinion in Application No. PCT/CN2016/087780, dated Mar. 29, 2017, 8 pages.
(Continued)

*Primary Examiner* — Philip R Wiest
(74) *Attorney, Agent, or Firm* — Fish & Richardson P.C.

(57) ABSTRACT

The present disclosure describes a kit for peritoneal dialysis that includes at least two bags. The kit also includes an overwrap for accommodating the at least two bags. At least one bag of the at least two bags forms at least a portion of the overwrap. According to the present disclosure, it is advantageously possible to reduce the material consumption of the overwrap, lower the cost of the kit, and reduce the amount of the disposable waste.

13 Claims, 4 Drawing Sheets

(56) References Cited

U.S. PATENT DOCUMENTS

| | | | |
|---|---|---|---|
| 6,508,800 B1 * | 1/2003 | Keilman | A61M 1/1668 604/410 |
| 10,507,275 B2 | 12/2019 | Herrenbauer et al. | |
| 2004/0102728 A1 | 5/2004 | Foster | |
| 2007/0149914 A1 * | 6/2007 | Axelsson | A61M 1/287 604/6.15 |

FOREIGN PATENT DOCUMENTS

| | | |
|---|---|---|
| CN | 1717258 | 1/2006 |
| CN | 1893991 | 1/2007 |
| CN | 102481401 | 5/2012 |
| CN | 103429213 | 12/2013 |
| CN | 203802866 | 9/2014 |
| CN | 211536207 | 9/2020 |
| JP | H10-28720 | 2/1998 |
| WO | WO 97/41902 | 11/1997 |
| WO | WO 2004/069307 | 8/2004 |
| WO | WO 2012/118060 | 9/2012 |
| WO | WO 2018/098806 | 6/2018 |

OTHER PUBLICATIONS

International Preliminary Report on Patentability in Application No. PCT/CN2016/087780, dated Jan. 1, 2019, 4 pages.
Extended European Search Report in European Appln. No. EP 16906684.2, dated Jan. 30, 2020, 7 pages.

* cited by examiner

KIT COMPRISING AT LEAST TWO BAGS

CROSS-REFERENCE TO RELATED APPLICATIONS

The present application is the national stage entry of International Patent Application No. PCT/CN2016/087780, filed on Jun. 29, 2016, the disclosure of which is incorporated herein by reference.

FIELD OF THE INVENTION

The disclosure relates to a kit comprising at least two bags, in particular a kit for peritoneal dialysis.

BACKGROUND

Due to high flexibility and convenience, peritoneal dialysis is used widely to treat kidney disease, chronic renal failure and toxic disease. Peritoneal dialysis is a dialysis therapy which uses a patient's peritoneum as a dialysis membrane, outstandingly improves the quality of patients' daily life and prolongs their residual renal function. By infusing a peritoneal dialysis fluid (fresh dialysate) into the patient's peritoneal cavity through a catheter implanted in the patient's body, osmosis and diffusion occur across the patient's peritoneum between the plasma of the patient and the peritoneal dialysis fluid. During peritoneal dialysis, waste such as metabolites or toxic substances and excess water diffuse from the plasma in the patient's capillary into the peritoneal dialysis fluid across the patient's peritoneum. At the same time, some substances which are required for normal functioning diffuse from the peritoneal dialysis fluid into the plasma in the patient's capillary across the patient's peritoneum. After a period of time, the peritoneal dialysis fluid containing waste and excess water is drained out of the patient's peritoneal cavity through the catheter and the fresh peritoneal dialysis fluid is then infused into the patient's peritoneal cavity through the catheter. This process of emptying and filling is repeated periodically to remove waste and excess water normally removed by the patient's kidneys and to aid in the regulation of fluid and electrolyte balance.

SUMMARY

In some embodiments, a kit includes at least two bags and an overwrap for accommodating the at least two bags. The at least two bags forms at least a portion of the overwrap.

The overwrap of the kit may consume less packaging materials and thus results in less medical waste. Additionally, the overwrap may improve heat penetration when the kit is sterilized after packaging. Considering huge volumes of the kits consumed by PD patients worldwide, the kit for peritoneal dialysis may lower the cost for peritoneal dialysis treatment and therefore offers a more affordable therapy.

These and other objects, features and characteristics, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE FIGURES

Figure 1:
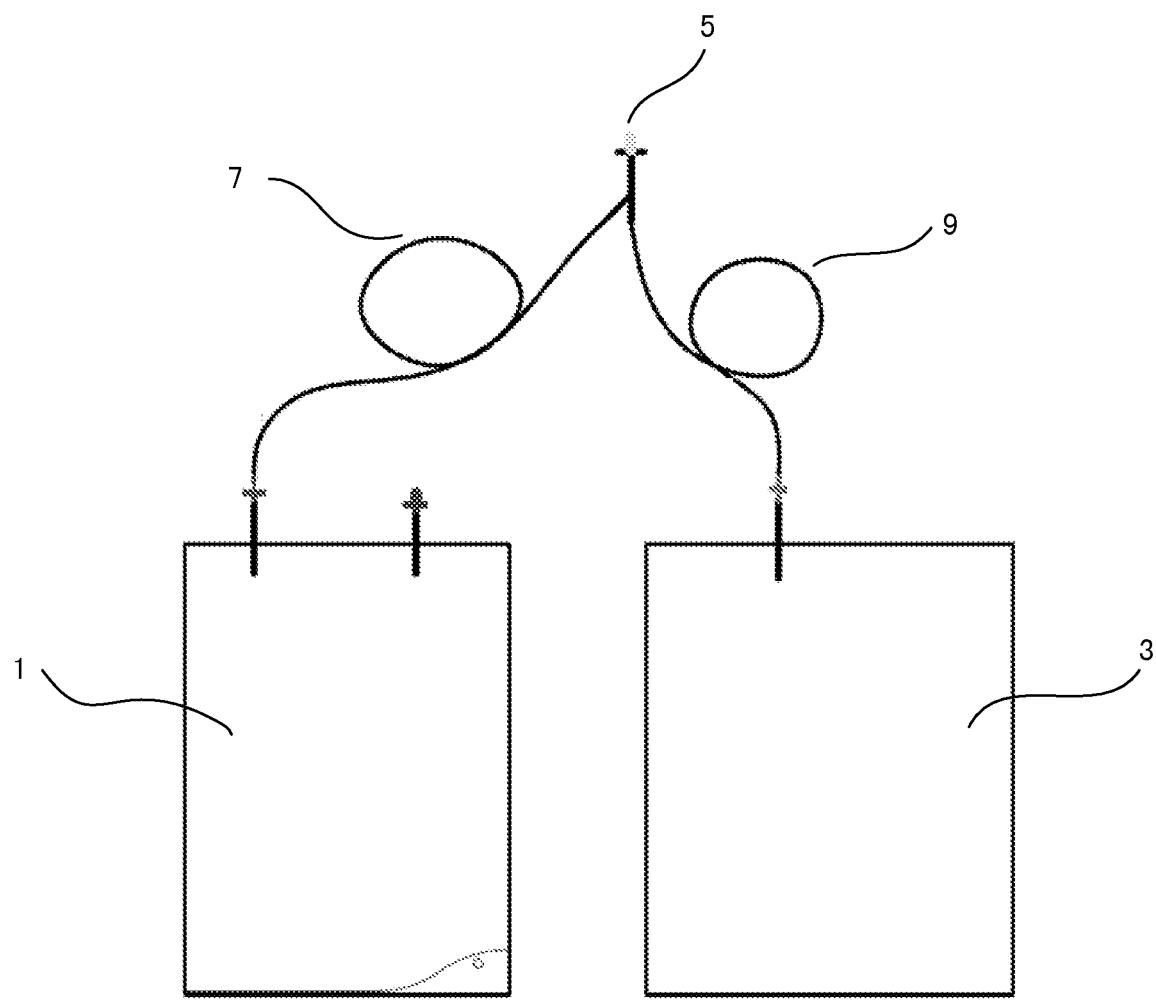
FIG. 1 shows schematically a conventional kit for peritoneal dialysis without an overwrap.

FIG. 1 shows schematically a kit for peritoneal dialysis. The kit may be used in Continuous Ambulatory Peritoneal Dialysis (CAPD). As shown in FIG. 1, the kit for peritoneal dialysis comprises a solution bag 1 filled with fresh peritoneal dialysis fluid for infusion, a drainage bag 3 for receiving the used peritoneal dialysis fluid drained out of the patient's peritoneal cavity, a patient connector 5 for establishing connection with the catheter implanted in the patient's body, a first transfer tubing 7 for communicating the solution bag 1 with the patient connector 5, and a second transfer tubing 9 for communicating the drainage bag 3 with the patient connector 5. Prior to being distributed to the patient, the kit for peritoneal dialysis must be packaged and sterilized to reduce potential patient infection and contamination caused by foreign matters. Thus, the kit for peritoneal dialysis further comprises an overwrap 10 within which the solution bag 1, the drainage bag 3, the patient connector 5, the first transfer tubing 7, and the second transfer tubing 9, are packaged.

Figure 2A:
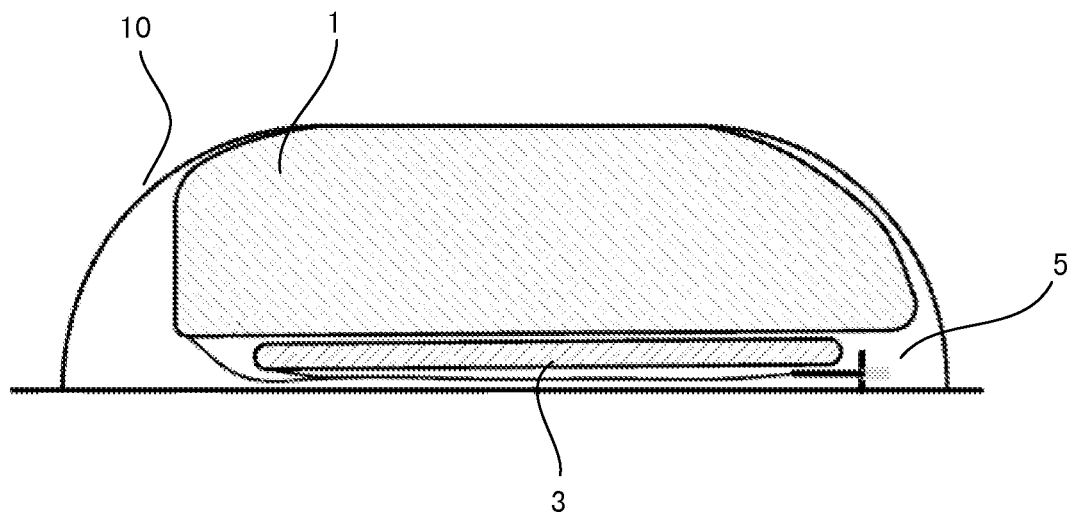
FIG. 2a is a side view showing the conventional kit for peritoneal dialysis in a packaged configuration.
Figure 2B:
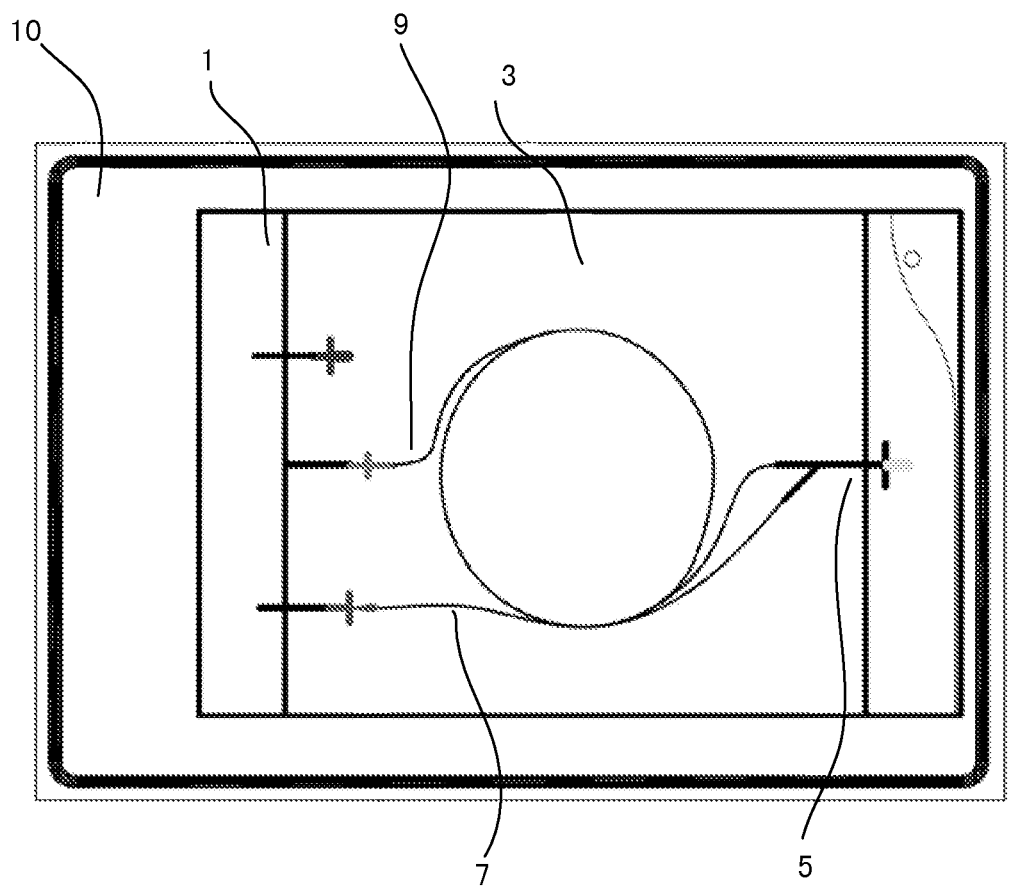
FIG. 2b is a top view showing the conventional kit for peritoneal dialysis.
Figure 3A:
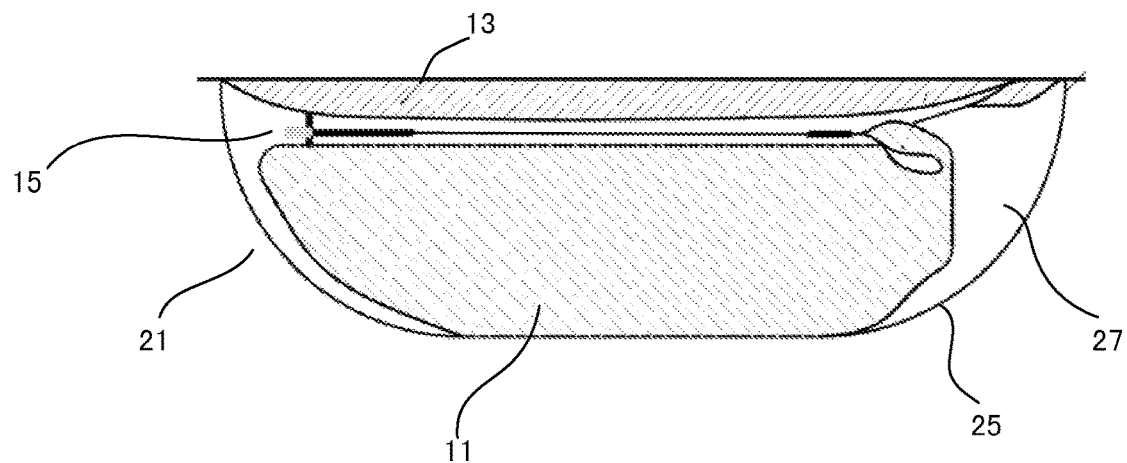
FIG. 3a is a side view showing a kit for peritoneal dialysis in a packaged configuration.
Figure 3B:
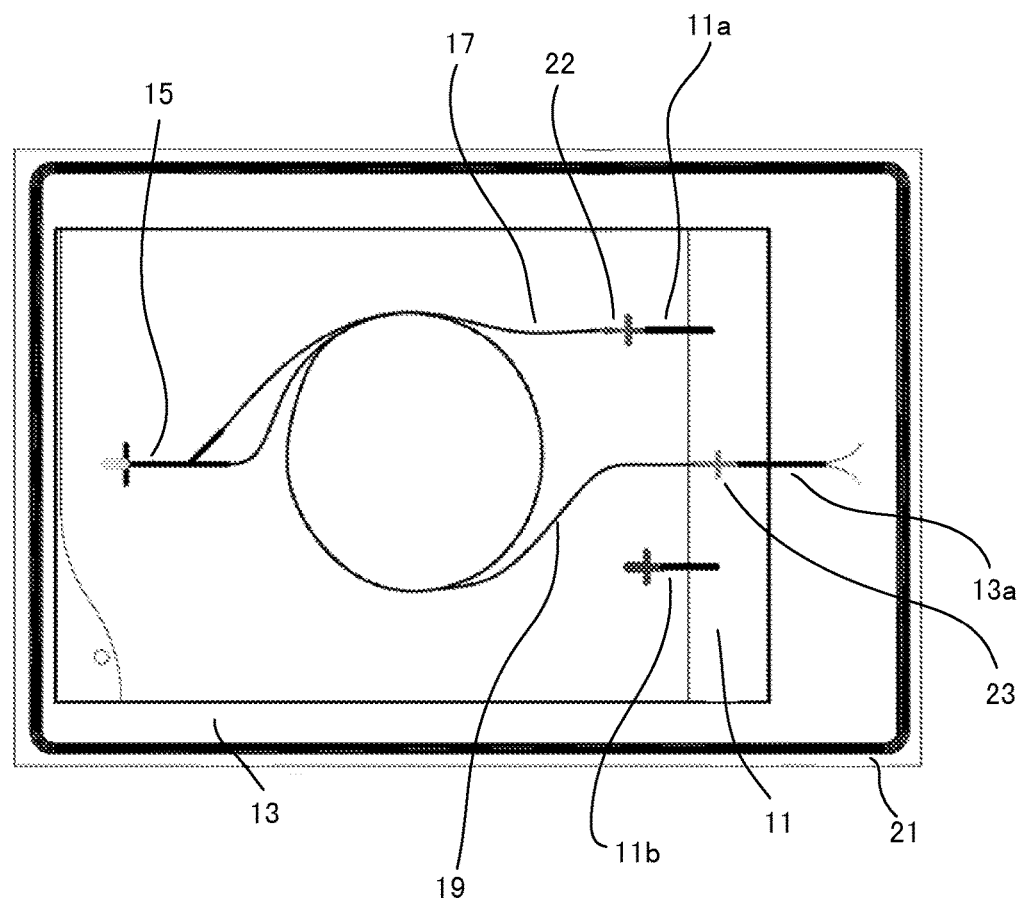
FIG. 3b is a top view showing the kit for peritoneal dialysis.

FIG. 2a is a side view showing a conventional kit for peritoneal dialysis in a packaged configuration, and FIG. 2b is a top view showing the conventional kit for peritoneal dialysis. As shown in FIGS. 2a and 2b, the overwrap 10 is in form of a pouch. The pouch may be comprised of a single piece or multiple pieces of film that are joined by a sealing process. The film(s) may be thermoformed and sealed using a manufacturing process such as Multi-vac. FIG. 3a is a side view showing a kit for peritoneal dialysis in a packaged configuration, and FIG. 3b is a top view showing the kit for peritoneal dialysis. As shown in FIGS. 3a and 3b, a kit for peritoneal dialysis generally comprises a solution bag 11 filled with fresh peritoneal dialysis fluid for infusion, an empty drainage bag 13 for receiving used peritoneal dialysis fluid drained out of the patient's peritoneal cavity, a patient connector 15 such as a Y-type luer connector for establishing connection with a catheter (not shown) implanted in the patient's body, a first transfer tubing 17 for communicating the solution bag 11 with the patient connector 15, a second transfer tubing 19 for communicating the drainage bag 13 with the patient connector 15, and an overwrap 21. The solution bag 11, the patient connector 15, the first transfer tubing 17, and the second transfer tubing 19 are packaged within the overwrap 21. The first transfer tubing 17 is connected at one end to an outlet port 11a of the solution bag 11 via a frangible connector 22. The transfer tubing is also connected to the patient connector 15 at other end. The second transfer tubing 19 is connected at one end to an inlet port 13a of the drainage bag 13 via a linking connector 23. The second transfer tubing is also connected to the patient connector 15 at other end. Preferably, the solution bag 11 further comprises an injection port 11b for injecting a supplementary liquid such as medicine or nutrient solution into the solution bag 11.

The drainage bag 13 stacks over the solution bag 11. A package film 25 covering the solution bag 11 from the bottom of the solution bag 11 is bonded hermetically to a periphery of the drainage bag 13 by a conventional process such as heat fusion. In this way, the drainage bag 13 and the package film 25 covering the solution bag 11 together form the overwrap 21. Although in the embodiment shown in FIGS. 3a and 3b the patient connector 15, the first transfer tubing 17, and the second transfer tubing 19 are sandwiched between the solution bag 11 and the drainage bag 13, the patient connector 15, the first transfer tubing 17, and the second transfer tubing 19 may be disposed between the solution bag 11 and the package film 25, or within a space 27 defined by the solution bag 11, the drainage bag 13 and the package film 25.

Figure 4A:
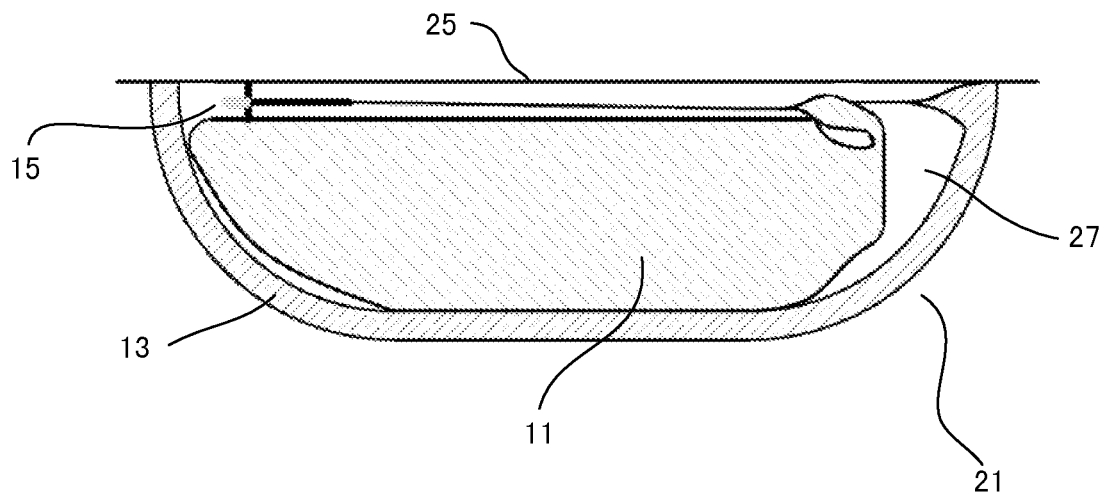
FIG. 4a is a side view showing a kit for peritoneal dialysis according to an alternative embodiment in a packaged configuration.
Figure 4B:
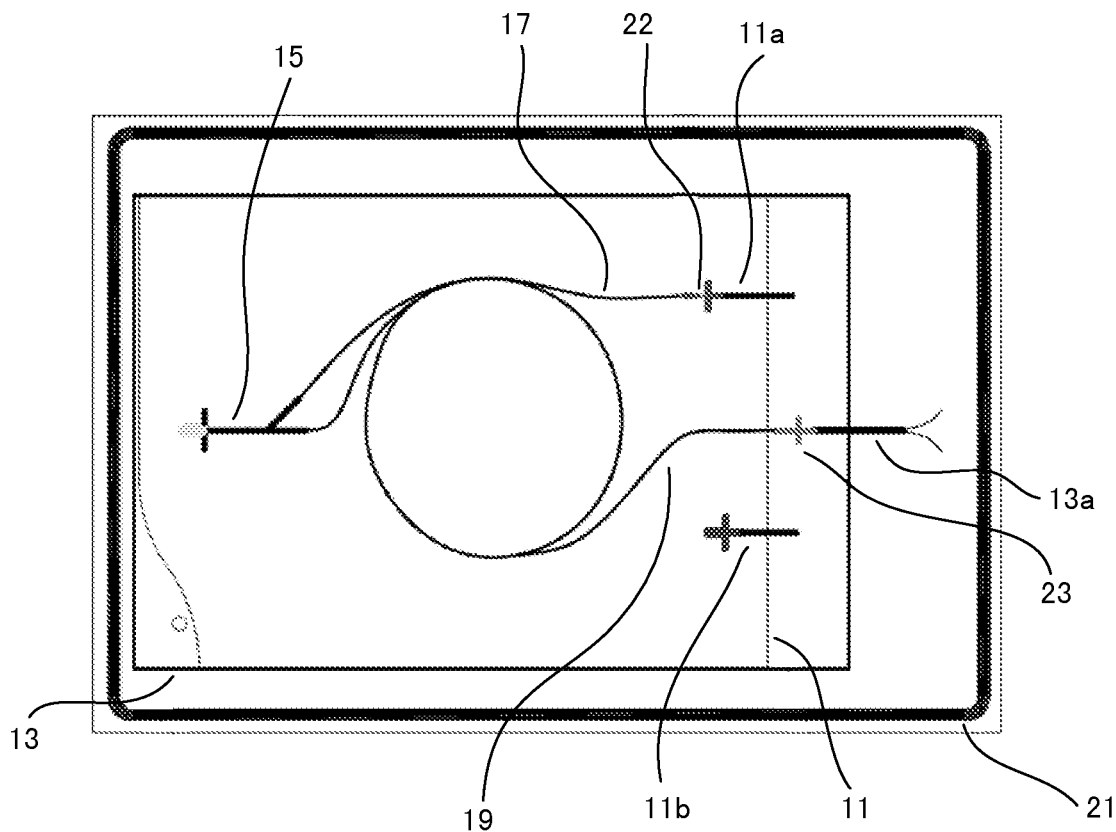
FIG. 4b is a top view showing the kit for peritoneal dialysis according to the alternative embodiment.

FIG. 4a is a side view showing a kit for peritoneal dialysis according to an alternative embodiment in a packaged configuration. FIG. 4b is a top view showing the kit for peritoneal dialysis according to the alternative embodiment. As an alternative, the solution bag 11 stacks over the drainage bag 13 and the drainage bag 13 is folded to surround partially the solution bag 11. The package film 25 disposed adjacent the top of the solution bag 11 is bonded hermetically to the periphery of the drainage bag 13. Similarly, the drainage bag 13 and the package film 25 disposed adjacent the top of the solution bag 11 together form the overwrap 21. Although in the embodiment shown in FIGS. 4a and 4b the patient connector 15, the first transfer tubing 17 and the second transfer tubing 19 are sandwiched between the solution bag 11 and the package film 25, the patient connector 15, the first transfer tubing 17 and the second transfer tubing 19 may be disposed between the solution bag 11 and the drainage bag 13 or within a space 27 defined by the solution bag 11, the drainage bag 13 and the package film 25.

The solution bag 11 and the drainage bag 13 are commonly made from films composed of PVC or olefinic based polymers which commonly contains a thermoplastic (e.g. polypropylene (PP)) and elastomer (e.g. styrene ethylene butadiene styrene (SEBS)). The package film 25 is commonly made from materials composed of high density polyethylene (HDPE), polypropylene (PP), or other olefinic based polymers. Of course, to lower the cost, the material from which the drainage bag is made may differ from that of the solution bag and/or of the overwrap. These films forming the solution bag, the drainage bag, and the package film can be extruded in mono-layer or multi-layer formats. To integrate the drainage bag 13 with the package film 25 to form the whole overwrap 21, the materials from which the drainage bag 13 and the package film 25 may be selected so that they not only satisfy the technical requirements from both the drainage bag and the overwrap, but also are compatible with bonding to each other to achieve an integrated design.

In use, the overwrap 21 and thus the package film 25, is torn off and removed. The patient connector 15 is connected with the catheter implanted in the patient's body. The used peritoneal dialysis fluid drains out of the patient's peritoneal cavity and flows into the drainage bag 13 through the patient connector 15 and the second transfer tubing 19. The drainage bag 13 filled with the used peritoneal dialysis fluid is removed. Then, the fresh peritoneal dialysis fluid is infused into the patient's peritoneal cavity from the solution bag 11 through the first transfer tubing 17 and the patient connector 15 by pinching a frangible point at the frangible connector 22 to open the frangible connector 22. After the fresh peritoneal dialysis fluid is infused into the patient's peritoneal cavity, the patient connector 15 is disconnected from the catheter implanted in the patient's body. This process of emptying and filling is completed and the kit for peritoneal dialysis is disposed as medical waste.

Although the drainage bag 13 forms the whole top of the overwrap 21 in the embodiment as shown in FIGS. 3a and 3b and the drainage bag 13 forms the whole bottom and the sides of the overwrap 21 in the alternative embodiment as shown in FIGS. 4a and 4b, it should be understood that the drainage bag 13 may occupy more or less portion of the overwrap 21.

The drainage bag 13 forms a portion of the whole overwrap 21. As a result, the material consumption of the package film 25, and thus the amount of the disposable medical waste after treatment, may be reduced. Further, due to the thinner thickness of the kit for peritoneal dialysis, heat penetration during sterilization may be increased, thereby further reducing the manufacturing costs of the kit for peritoneal dialysis. Considering huge volumes of the kits consumed by PD patients worldwide, the kit for peritoneal dialysis as described herein ideally lowers the cost for peritoneal dialysis treatment and therefore offers a more affordable therapy especially for emerging market.

Although in the preferred embodiments only the drainage bag is shown to form a portion of the overwrap, it is feasible that the solution bag forms a portion of the overwrap or both the drainage bag and the solution bag form a portion of the overwrap or the whole overwrap. Further, in the preferred embodiments, the kit for peritoneal dialysis comprises only one solution bag. However, other solution other than peritoneal dialysis fluid may also be required to infuse into the patient for some therapy. In such case, the kit for peritoneal dialysis may comprise more than one solution bag. Although in the preferred embodiments the kit is implemented as a kit for peritoneal dialysis, it should be understood that the kit may be any kit comprising at least two bags one of which forms a portion of the overwrap of the kit whether at least one of the bags is filled with liquid or not.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

The invention claimed is:

1. A kit for peritoneal dialysis comprising:
   at least two bags comprising:
      at least one solution bag configured to contain peritoneal dialysis fluid for infusion; and
      a drainage bag configured to receive used peritoneal dialysis fluid; and
   an overwrap,
   wherein the drainage bag and a package film together form the overwrap so that the at least one solution bag is enclosed by the overwrap.

2. The kit according to claim 1, wherein the drainage bag stacks over the solution bag, and wherein the package film covering the solution bag from the bottom of the solution bag is bonded hermetically to a periphery of the drainage bag.

3. The kit according to claim 2, wherein: (i) a patient connector configured to establish a connection with a catheter, (ii) a first transfer tubing configured to connect the solution bag with the patient connector such that the solution bag and patient connector are in fluid communication, and (iii) a second transfer tubing configured to connect the drainage bag with the patient connector such that the drainage bag and patient connector are in fluid communication, are each disposed between the solution bag and the drainage bag.

4. The kit according to claim 3, wherein the first transfer tubing is connected to an outlet port of the solution bag via a frangible connector.

5. The kit according to claim 4, wherein the catheter is configured to be implanted in a patient.

6. The kit according to claim 3, wherein the second transfer tubing is connected to an inlet port of the drainage bag via a linking connector.

7. The kit according to claim 2, wherein at least one of the solution bag, packaging film, or the drainage bag, is formed by a film, wherein the film is extruded as a monolayer or multilayer format.

8. The kit according to claim 1, wherein the solution bag stacks over the drainage bag and is surrounded at least partially by the drainage bag, and wherein the package film disposed adjacent a top of the solution bag is bonded hermetically to a periphery of the drainage bag.

9. The kit according to claim 8, wherein a patient connector configured to establish a connection with a catheter, a first transfer tubing configured to connect the solution bag with the patient connector such that the solution bag and patient connector are in fluid communication, and a second transfer tubing configured to connect the drainage bag with the patient connector such that the drainage bag and patient connector are in fluid communication, are each sandwiched between the solution bag and the package film.

10. The kit according to claim 9, wherein the first transfer tubing is connected to an outlet port of the solution bag via a frangible connector.

11. The kit according to claim 9, wherein the second transfer tubing is connected to an inlet port of the drainage bag via a linking connector.

12. The kit according to claim 1, wherein the material from which the drainage bag is made differs from that of the solution bag and of the overwrap.

13. The kit according to claim 1, wherein the material from which the drainage bag is made differs from that of the solution bag or of the overwrap.

\* \* \* \* \*